(12) United States Patent
Macht et al.

(10) Patent No.: US 9,700,876 B2
(45) Date of Patent: Jul. 11, 2017

(54) MECHANICALLY STABLE HOLLOW CYLINDRICAL SHAPED CATALYST BODIES FOR GAS PHASE OXIDATION OF AN ALKENE TO AN UNSATURATED ALDEHYDE AND/OR AN UNSATURATED CARBOXYLIC ACID

(71) Applicant: BASF SE, Ludwigshafen (DE)

(72) Inventors: Josef Macht, Ludwigshafen (DE); Christian Walsdorff, Ludwigshafen (DE); Cornelia Katharina Dobner, Ludwigshafen (DE); Stefan Lipp, Karlsruhe (DE); Cathrin Alexandra Welker-Nieuwoudt, Birkenheide (DE); Ulrich Hammon, Mannheim (DE); Holger Borchert, Offstein (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/535,743

(22) Filed: Nov. 7, 2014

(65) Prior Publication Data

US 2015/0133686 A1    May 14, 2015

(30) Foreign Application Priority Data

Nov. 11, 2013 (EP) ..................... 13192277

(51) Int. Cl.
| | |
|---|---|
| *B01J 23/00* | (2006.01) |
| *B01J 23/28* | (2006.01) |
| *B01J 23/881* | (2006.01) |
| *B01J 23/887* | (2006.01) |
| *B01J 35/00* | (2006.01) |
| *B01J 35/02* | (2006.01) |
| *B01J 35/04* | (2006.01) |
| *C01G 39/00* | (2006.01) |
| *B01J 23/888* | (2006.01) |
| *C07C 45/35* | (2006.01) |
| *C07C 51/25* | (2006.01) |
| *B01J 37/08* | (2006.01) |
| *B01J 37/00* | (2006.01) |
| *C04B 35/495* | (2006.01) |
| *C04B 35/626* | (2006.01) |

(Continued)

(52) U.S. Cl.
CPC ......... *B01J 23/8885* (2013.01); *B01J 23/002* (2013.01); *B01J 23/8876* (2013.01); *B01J 35/0006* (2013.01); *B01J 35/023* (2013.01); *B01J 35/026* (2013.01); *B01J 35/04* (2013.01); *B01J 37/0009* (2013.01); *B01J 37/08* (2013.01); *C01G 49/0036* (2013.01); *C01G 51/00* (2013.01); *C01G 53/00* (2013.01); *C04B 35/495* (2013.01); *C04B 35/6261* (2013.01); *C04B 35/62655* (2013.01); *C04B 35/62675* (2013.01); *C04B 35/62685* (2013.01); *C04B 35/64* (2013.01); *C07C 45/35* (2013.01); *C07C 51/252* (2013.01); *B01J 35/0026* (2013.01); *B01J 37/0045* (2013.01); *B01J 37/04* (2013.01); *B01J 2523/00* (2013.01); *C01P 2002/72* (2013.01); *C01P 2004/61* (2013.01); *C01P 2004/62* (2013.01); *C01P 2004/64* (2013.01); *C01P 2006/12* (2013.01); *C01P 2006/14* (2013.01); *C04B 2235/3201* (2013.01); *C04B 2235/326* (2013.01); *C04B 2235/3256* (2013.01); *C04B 2235/3275* (2013.01); *C04B 2235/3298* (2013.01); *C04B 2235/44* (2013.01); *C04B 2235/443* (2013.01); *C04B 2235/5409* (2013.01); *C04B 2235/5427* (2013.01); *C04B 2235/5436* (2013.01); *C04B 2235/5445* (2013.01); *C04B 2235/604* (2013.01); *C04B 2235/608* (2013.01); *C04B 2235/656* (2013.01); *C04B 2235/72* (2013.01); *C04B 2235/95* (2013.01)

(58) Field of Classification Search
None
See application file for complete search history.

(56) References Cited

U.S. PATENT DOCUMENTS

| | | | |
|---|---|---|---|
| 4,366,093 A | 12/1982 | Shiozaki et al. | |
| 4,438,217 A | 3/1984 | Takata et al. | |

(Continued)

FOREIGN PATENT DOCUMENTS

| | | |
|---|---|---|
| DE | 33 38 380 A1 | 4/1984 |
| DE | 44 07 020 A1 | 9/1994 |

(Continued)

OTHER PUBLICATIONS

U.S. Appl. No. 14/737,025, filed Jun. 11, 2015, Hammon, et al.

(Continued)

*Primary Examiner* — Colin W Slifka
(74) *Attorney, Agent, or Firm* — Oblon, McClelland, Maier & Neustadt, L.L.P.

(57) ABSTRACT

A hollow cylindrical shaped catalyst body for gas phase oxidation of an alkene to an α,β-unsaturated aldehyde and/or an α,β-unsaturated carboxylic acid comprises a compacted multimetal oxide having an external diameter ED, an internal diameter ID and a height H, wherein ED is in the range from 3.5 to 4.5 mm; the ratio q=ID/ED is in the range from 0.4 to 0.55; and the ratio p=H/ED is in the range from 0.5 to 1. The shaped catalyst body is mechanically stable and catalyzes the partial oxidation of an alkene to the products of value with high selectivity. It provides a sufficiently high catalyst mass density of the catalyst bed and good long-term stability with acceptable pressure drop.

16 Claims, No Drawings

(51) Int. Cl.
*C04B 35/64* (2006.01)
*C01G 49/00* (2006.01)
*C01G 51/00* (2006.01)
*C01G 53/00* (2006.01)
*B01J 37/04* (2006.01)

(56) References Cited

U.S. PATENT DOCUMENTS

| | | | |
|---|---|---|---|
| 4,538,874 A | 9/1985 | Dambach et al. | |
| 4,656,157 A | 4/1987 | Hofmann et al. | |
| 5,144,091 A | 9/1992 | Martan et al. | |
| 5,449,821 A * | 9/1995 | Neumann | B01J 23/002 562/546 |
| 5,521,137 A * | 5/1996 | Martin | B01J 23/002 502/211 |
| 5,569,636 A * | 10/1996 | Martin | B01J 23/002 502/211 |
| 5,583,084 A * | 12/1996 | Martin | B01J 23/002 502/211 |
| 5,583,086 A | 12/1996 | Tenten et al. | |
| 5,739,391 A | 4/1998 | Ruppel et al. | |
| 5,821,390 A | 10/1998 | Ruppel et al. | |
| 6,252,122 B1 * | 6/2001 | Tenten | B01J 23/31 502/244 |
| 6,333,011 B1 | 12/2001 | Schliephake et al. | |
| 6,395,936 B1 | 5/2002 | Arnold et al. | |
| 6,525,217 B1 | 2/2003 | Unverricht et al. | |
| 7,534,339 B2 | 5/2009 | Matsumoto et al. | |
| 8,173,838 B2 * | 5/2012 | Takeda | C07C 45/38 562/532 |
| 8,546,295 B2 * | 10/2013 | Raichle | B01J 23/002 502/311 |
| 8,785,344 B2 | 7/2014 | Karpov et al. | |
| 2004/0015013 A1 | 1/2004 | Hammon et al. | |
| 2004/0034249 A1 | 2/2004 | Arnold et al. | |
| 2004/0171874 A1 | 9/2004 | Watanabe et al. | |
| 2004/0192965 A1 | 9/2004 | Petzoldt et al. | |
| 2004/0242926 A1 | 12/2004 | Dieterle et al. | |
| 2005/0038291 A1 | 2/2005 | Petzoldt et al. | |
| 2005/0065371 A1 | 3/2005 | Petzoldt et al. | |
| 2005/0131253 A1 | 6/2005 | Teshigahara et al. | |
| 2007/0003076 A1 | 1/2007 | Croft, III | |
| 2007/0032377 A1 | 2/2007 | Hibst et al. | |
| 2007/0032680 A1 | 2/2007 | Felder et al. | |
| 2008/0076838 A1 | 3/2008 | Puppe | |
| 2008/0177105 A1 | 7/2008 | Raichle et al. | |
| 2010/0010238 A1 | 1/2010 | Eger et al. | |
| 2011/0017348 A1 | 1/2011 | Tanimoto et al. | |
| 2011/0065953 A1 | 3/2011 | Cremer et al. | |
| 2011/0130596 A1 | 6/2011 | Macht et al. | |
| 2011/0295041 A1 | 12/2011 | Wang et al. | |
| 2013/0023699 A1 | 1/2013 | Macht et al. | |
| 2014/0018572 A1 | 1/2014 | Welker-Nieuwoudt et al. | |
| 2014/0221683 A1 | 8/2014 | Welker-Nieuwoudt et al. | |

FOREIGN PATENT DOCUMENTS

| | | |
|---|---|---|
| DE | 44 31 957 A1 | 3/1995 |
| DE | 199 10 506 A1 | 9/2000 |
| DE | 199 48 523 A1 | 4/2001 |
| DE | 100 46 957 A1 | 4/2002 |
| DE | 100 49 873 A1 | 4/2002 |
| DE | 101 01 695 A1 | 7/2002 |
| DE | 10232748 | 7/2002 |
| DE | 103 36 386 A1 | 3/2004 |
| DE | 103 44 149 A1 | 4/2004 |
| DE | 103 13 208 A1 | 10/2004 |
| DE | 103 13 213 A1 | 10/2004 |
| DE | 103 37 788 A1 | 10/2004 |
| DE | 10 2006 044 520 A1 | 4/2008 |
| DE | 10 2007 005 606 A1 | 4/2008 |
| DE | 10 2007 003 076 A1 | 7/2008 |
| DE | 10 2007 004 961 A1 | 7/2008 |
| DE | 10 2008 040 093 A1 | 12/2008 |
| DE | 10 2008 042 060 A1 | 6/2009 |
| DE | 10 2009 047 291 A1 | 9/2010 |
| EP | 0 184 790 A2 | 6/1986 |
| EP | 0 468 290 A1 | 1/1992 |
| EP | 0 575 897 A1 | 12/1993 |
| EP | 0 700 714 A1 | 3/1996 |
| EP | 0 700 893 A1 | 3/1996 |
| EP | 0 873 783 A1 | 10/1998 |
| EP | 1 106 598 A2 | 6/2001 |
| EP | 1 270 065 A1 | 1/2003 |
| WO | WO 02/24620 A2 | 3/2002 |
| WO | WO 2005/030393 A1 | 4/2005 |
| WO | WO 2007/017431 A1 | 2/2007 |
| WO | WO 2007/082827 A1 | 7/2007 |
| WO | WO 2008/087116 A1 | 7/2008 |

OTHER PUBLICATIONS

U.S. Appl. No. 14/536,969, filed Nov. 10, 2014, Macht, et al.
U.S. Appl. No. 14/487,383, filed Sep. 16, 2014, Welker-Nieuwoudt, et al.
International Search Report issued Apr. 15, 2015 in PCT/EP2014/073820.

* cited by examiner

MECHANICALLY STABLE HOLLOW CYLINDRICAL SHAPED CATALYST BODIES FOR GAS PHASE OXIDATION OF AN ALKENE TO AN UNSATURATED ALDEHYDE AND/OR AN UNSATURATED CARBOXYLIC ACID

The present invention relates to hollow cylindrical shaped catalyst bodies for gas phase oxidation of an alkene to an $\alpha,\beta$-unsaturated aldehyde and/or an $\alpha,\beta$-unsaturated carboxylic acid, comprising a compacted multimetal oxide having an external diameter ED, an internal diameter ID and a height H. The present invention also relates to processes for producing hollow cylindrical shaped catalyst bodies, and to the use thereof as catalysts for the heterogeneously catalyzed partial gas phase oxidation of organic compounds, especially that of propene to acrolein as the main product and acrylic acid as the by-product.

At present, the preparation of $\alpha,\beta$-unsaturated aldehydes and/or $\alpha,\beta$-unsaturated carboxylic acids on the industrial scale, especially of acrolein and acrylic acid, is effected essentially by heterogeneously catalyzed partial oxidation of alkenes (see, for example, DE-A 103 36 386 regarding preparation of acrylic acid by partial oxidation of propene).

Hollow cylinders are known as a suitable geometry for shaped catalyst bodies.

U.S. Pat. No. 4,366,093 discloses hollow cylindrical shaped catalyst bodies having an external diameter of 3 to 6 mm, an internal diameter of at least 1.0 mm, a wall thickness of at most 1.5 mm and a height of 3 to 6 mm. There is also specific disclosure of a hollow cylindrical molded catalyst having an external diameter of 4 mm, an internal diameter of 1.8 mm and a height of 3 mm. The hollow cylindrical molded catalysts disclosed comprise sintered alumina, from which shaped catalyst bodies which comprised 18% by weight of copper chloride and 1.5% by weight of potassium chloride were obtained by means of impregnation. These shaped catalyst bodies were used for oxychlorination of ethene.

The use of hollow cylindrical shaped catalyst bodies was also proposed in the prior art for processes for gas phase oxidation of alkenes to $\alpha,\beta$-unsaturated aldehydes and $\alpha,\beta$-unsaturated carboxylic acids.

U.S. Pat. No. 4,438,217 discloses the use of hollow cylindrical shaped catalyst bodies comprising a multimetal oxide for gas phase oxidation of propene to acrolein. A particular catalyst disclosed has an external diameter of 4 mm, an internal diameter of 1.0 mm, a height of 4.4 mm and a wall thickness of 2 mm. Through the use of hollow cylindrical shaped catalyst bodies, it was possible to achieve an elevated selectivity and activity, a low pressure drop and improved heat transfer compared to solid cylindrical shaped catalyst bodies having the same external diameter and height.

DE 101 01 695 A1 describes a process for heterogeneously catalyzed gas phase partial oxidation of a precursor compound of (meth)acrylic acid in a fixed catalyst bed comprising a mixed oxide active composition shaped to a geometric body, wherein at least one cavity has been incorporated into the surface of the geometric body and the ratio of the volume of the geometric body to the volume of the underlying geometric base body is not more than 0.63 and the ratio of the surface area of the body to the volume of the body is at least 22 $cm^{-1}$. The use of hollow cylindrical shaped catalyst bodies comprising a multimetal oxide, especially of those having external diameter×height×internal diameter of 5.5×3×3.5 mm (wall thickness 1 mm), 6×3×4 mm (wall thickness 1 mm), 7×3×4.5 mm (wall thickness 1.25 mm), 7×3×5 mm (wall thickness 1 mm), is described as preferred.

The shaped catalyst bodies in accordance with the teachings of DE 101 01 695 A1, when used in a process for heterogeneously catalyzed oxidation of propene, led to an improved selectivity of formation of products of value, i.e. the formation of acrolein and acrylic acid.

The reason for the observed influences of the shaped body dimensions on the selectivity and rate of the heterogeneously catalyzed oxidation in the gas phase is probably limitation by what are called inner transport influences. In this context, it is not the actual conversion of the reactants over the active sites in the interior of the pore structure that limits the reaction rate; instead, the diffusion rate of the reactants in the pore structure of the catalyst, i.e. the transport of the reactants to the active sites, is the limiting step. This mass transfer limitation can be reduced by decreasing the characteristic diffusion length. Shaped catalyst bodies having a high ratio of the surface area of the body to the volume of the body lead to a reduction in the characteristic diffusion length. The ratio of the surface area to the volume of a hollow cylindrical shaped catalyst body can be lowered, inter alia, by reducing the wall thickness.

It is all the more noticeable that, for processes for gas phase oxidation of an alkene to an $\alpha,\beta$-unsaturated aldehyde and/or an $\alpha,\beta$-unsaturated carboxylic acid, no hollow cylindrical shaped catalyst bodies which comprise a multimetal oxide and have similar dimensions to the supported catalysts described in U.S. Pat. No. 4,366,093 for the oxychlorination of ethylene have been disclosed. Exclusively geometries with thicker walls, greater external diameter or greater height have been described.

Especially with regard to the wall thickness, which is critical for transport phenomena, even the thinnest-wall catalyst geometry disclosed in U.S. Pat. No. 4,438,217, having a thicker wall, is distinctly inferior to the thinnest-wall embodiment disclosed in U.S. Pat. No. 4,366,093 for supported catalysts. Thus, correspondingly thick-wall ring tablets became characteristic of the prior art in processes for oxidation of propene, as found by way of example in DE 103 44 149 A1. Contributory factors to this development in the technical teaching may have been various assessments, ideas or concerns. In this context, it is necessary to consider questions of the pressure drop of a catalyst bed or of the mechanical stability of the shaped bodies. Especially in the case of catalysts which have been produced by compaction or tableting of pulverulent precursors, however, there are limits to this optimization, because shaped catalyst bodies having extremely thin walls do not have sufficient mechanical stability, and excessive fracturing occurs, for example, on introduction into the reaction tubes.

The advantageousness of a high ratio of the surface area of the body to the volume of the body ($\geq 22$ $cm^{-1}$) is known from DE 101 01 695 A1. The wall thickness of the hollow cylindrical shaped catalyst bodies of DE 101 01 695 A1 is in the range from 1 to 1.25 mm.

However, a disadvantage of the hollow cylindrical shaped catalyst bodies of DE 101 01 695 A1 is their low mechanical stability and the low catalyst mass density of the catalyst bed because of the low ratio of the volume of the geometric body to the volume of the underlying geometric base body ($\leq 0.63$). The low mechanical stability leads to high material losses in industrial scale catalyst production and, because of excessive fracturing in the filling of the reaction tubes, to yield losses because of inhomogeneous flow through the individual reaction tubes in the shell and tube reactor. The low catalyst mass density of the catalyst bed is disadvantageous because the higher reaction temperatures caused thereby lead to accelerated catalyst deactivation.

It is an object of the present invention to provide a mechanically stable shaped catalyst body which catalyzes the partial oxidation of an alkene to the α,β-unsaturated aldehyde and α,β-unsaturated carboxylic acid products of value with high selectivity. Another object is to provide shaped catalyst bodies which provide good long-term stability with acceptable pressure drop through a sufficiently high catalyst mass density of the catalyst bed.

We have now found that this object can be achieved by a hollow cylindrical shaped catalyst body for gas phase oxidation of an alkene to an α,β-unsaturated aldehyde and/or an α,β-unsaturated carboxylic acid, comprising a compacted multimetal oxide having an external diameter ED, an internal diameter ID and a height H, wherein
(i) ED is in the range from 3.5 to 4.5 mm;
(ii) the ratio q according to the following equation $$q = \frac{ID}{ED}$$

is in the range from 0.4 to 0.55;
and
(iii) the ratio p according to the following equation $$p = \frac{H}{ED}$$

is in the range from 0.5 to 1.

The hollow cylindrical shaped catalyst bodies have sufficient mechanical strength (fracture stability) in the course of reactor filling. A measure of the mechanical strength of the catalyst particles provided is the following drop test: 50 g of catalyst are allowed to fall through a vertical tube of length 3 m having an internal diameter of 23 mm. The catalyst falls into a porcelain dish directly underneath the tube and is separated from the dust and fractured material which arise on impact. The shaped catalyst bodies separated intact are weighed. The proportion of intact shaped catalyst bodies is determined by comparison of the mass determined here with the mass of the shaped catalyst bodies used for the drop test. The proportion of intact shaped catalyst bodies is a measure of the resistance of the shaped catalyst body to mechanical stress. The proportion of intact shaped catalyst bodies thus determined in the drop test is preferably at least 70%, more preferably at least 75%, further preferably at least 80%.

The side crushing strength of the hollow cylindrical shaped catalyst bodies is generally at least 4 N, preferably at least 6 N, more preferably at least 7 N. Typically, the side crushing strength of the hollow cylindrical shaped catalyst bodies is less than 23 N, usually less than 20 N, usually less than 14 N. The side crushing strength is more preferably 7 to 14 N. The experimental determination of the side crushing strength is conducted as described in documents WO 2005/030393 and WO 2007/017431.

The hollow cylindrical geometry of the present shaped catalyst bodies can be described by two cylinders of equal height and having coincident axes. One of the cylinders has a diameter ID. The other cylinder has a diameter ED. The outer surface of the inner cylinder coincides with the inner face of the hollow cylindrical shaped catalyst body. The outer surface of the outer cylinder coincides with the outer face of the hollow cylindrical shaped catalyst body.

The external diameter ED is preferably in the range from 3.6 to 4.4 mm, more preferably in the range from 3.7 to 4.3 mm, especially preferably in the range from 3.8 to 4.2 mm.

The quotient q corresponds to the ratio of the internal diameter of the hollow cylindrical shaped catalyst body to the external diameter of the hollow cylindrical shaped catalyst body. q is preferably selected within the range from 0.45 to 0.55.

The quotient p corresponds to the ratio of the height of the hollow cylindrical shaped catalyst body to the external diameter of the hollow cylindrical shaped catalyst body. p is preferably selected within the range from 0.60 to 0.95, more preferably within the range from 0.65 to 0.90.

The geometric volume of the hollow cylindrical shaped catalyst body is preferably 22 to 34 mm$^3$. The geometric volume can be calculated on the basis of the height H of the hollow cylinder, the external diameter ED and the internal diameter ID. A hollow cylinder having the dimensions ED=4 mm, H=3 mm and ID=2 mm, for example, has a geometric volume of 28.27 mm$^3$.

The ratio of geometric volume of the shaped catalyst body to the volume of the underlying geometric base body is preferably 0.7 to 0.85. The underlying geometric base body is regarded as being the geometric base body which encompasses the shaped catalyst body. The underlying geometric base body of a hollow cylinder is a solid cylinder having the same ED and the same H.

The ratio of the geometric surface area of the shaped catalyst body to the geometric volume of the shaped catalyst body, also referred to hereinafter as effective surface area, is preferably 22 to 32 cm$^{-1}$. The geometric surface area is an idealized parameter and does not take account of the increase in surface area caused by the porosity or surface roughness of the shaped body. The geometric surface area of the hollow cylindrical shaped catalyst bodies is calculated by the following formula:

$$\frac{\pi}{2}((ED)^2 - (ID)^2) + \pi(ED + ID)H$$

The density of the hollow cylindrical shaped catalyst body is preferably 1.2 to 2.0 g/cm$^3$. It is calculated by dividing the mass of the shaped catalyst body by the geometric volume thereof.

A low wall thickness WT of the hollow cylindrical shaped catalyst body is favorable, since this is accompanied by a high effective surface area of the shaped catalyst body, which leads to a reduction in the characteristic diffusion length and therefore to an elevated selectivity for products of value and elevated rate of target product formation. On the other hand, the wall thickness cannot be reduced arbitrarily, since the mechanical strength of the shaped catalyst bodies otherwise falls too significantly. Therefore, the value WT according to the following equation $$WT = \frac{ED - ID}{2}$$

is preferably selected within the range from 0.8 to 1.2 mm, preferably within the range from 0.8 to 1.1 mm, more preferably within the range from 0.85 to 1.05 mm.

A hollow cylindrical shaped catalyst body preferred in accordance with the invention has an external diameter in the range from 3.7 to 4.3 mm, a height in the range from 2.3 to 3.2 mm and an internal diameter in the range from 1.8 to 2.2 mm. A hollow cylindrical shaped catalyst body particularly preferred in accordance with the invention has an external diameter in the range from 3.9 to 4.1 mm, a height in the range from 2.9 to 3.1 mm and an internal diameter in the range from 1.9 to 2.1 mm. A hollow cylindrical shaped catalyst body very particularly preferred in accordance with the invention has an external diameter of 4 mm, a height of 3 mm and an internal diameter of 2 mm.

It is also possible for either both of or, as described in EP-A 184790 or U.S. Pat. No. 4,656,157, only one of the end faces of the hollow cylindrical shaped catalyst bodies to be curved, for example in such a way that the radius of curvature is preferably 0.4 to 5 times the external diameter E. Preferably in accordance with the invention, neither of the end faces is curved.

The hollow cylindrical shaped catalyst body comprises a compacted multimetal oxide. The hollow cylindrical shaped catalyst bodies preferably consist predominantly of the compacted multimetal oxide, especially to an extent of 80 to 100% by weight, further preferably to an extent of 85 to 100% by weight, more preferably to an extent of 90 to 100% by weight (so-called shaped unsupported catalyst bodies). In addition, the hollow cylindrical shaped catalyst body may especially comprise shaping aids, for example reinforcers. Particularly useful reinforcers are microfibers. The microfibers may consist, for example, of glass, asbestos, silicon carbide or potassium titanate. They have a beneficial effect on the integrity of the shaped body.

In addition, the hollow cylindrical shaped catalyst body may comprise lubricants, for example graphite. Preferred lubricants are graphite, carbon black, polyethylene glycol, stearic acid, starch, polyacrylic acid, mineral or vegetable oil, water, glycerol, cellulose ether, boron trifluoride and/or boron nitride. A particularly preferred lubricant is graphite. The aforementioned added amount is typically ≥0.5% by weight, usually ≥2.5% by weight. Inventive graphites added with preference are Timcal T44, Asbury 3160 and Asbury 4012. The lubricants escape wholly or partly in the form of gaseous compounds (e.g. CO, $CO_2$), especially in the course of calcination.

Multimetal oxides for gas phase oxidation of alkenes to α,β-unsaturated aldehydes and/or α,β-unsaturated carboxylic acids are known per se. A suitable multimetal oxide is therefore any capable of catalyzing this gas phase oxidation. Preferably, the multimetal oxide comprises at least the elements iron, bismuth and at least one of the elements molybdenum and tungsten, for example at least the elements molybdenum, iron and bismuth.

The multimetal oxide may correspond, for example, to the formula (I)

$$Mo_{12}Bi_aFe_bX^1_cX^2_dX^3_eX^4_fO_n \qquad (I)$$

in which
$X^1$ is nickel and/or cobalt,
$X^2$ is thallium, an alkali metal and/or an alkaline earth metal,
$X^3$ is zinc, phosphorus, arsenic, boron, antimony, tin, cerium, lead, vanadium, chromium and/or tungsten,
$X^4$ is silicon, aluminum, titanium and/or zirconium,
a is a number in the range from 0.2 to 5,
b is a number in the range from 0.01 to 10,
c is a number in the range from 0 to 10,
d is a number in the range from 0 to 2,
e is a number in the range from 0 to 8,
f is a number in the range from 0 to 10, and
n is a number which is determined by the valency and frequency of the elements other than oxygen in (I);
or correspond to the formula (II)

$$[Y^1_{a'}Y^2_{b'}O_{x'}]_p[Y^3_{c'}Y^4_{d'}Y^5_{e'}Y^6_{f'}Y^7_{g'}Y^8_{h'}O_{y'}]_q \qquad (II)$$

in which
$Y^1$ is bismuth or is bismuth and at least one of the elements tellurium, antimony, tin and copper,
$Y^2$ is molybdenum or tungsten, or is molybdenum and tungsten,
$Y^3$ is an alkali metal, thallium and/or samarium,
$Y^4$ is an alkaline earth metal, nickel, cobalt, manganese, zinc, tin, cadmium and/or mercury,
$Y^5$ is iron or is iron and at least one of the elements vanadium, chromium and cerium,
$Y^6$ is phosphorus, arsenic, boron, antimony and/or bismuth,
$Y^7$ is a rare earth metal, titanium, zirconium, niobium, tantalum, rhenium, ruthenium, rhodium, copper, silver, gold, aluminum, gallium, indium, silicon, germanium, lead, thorium and/or uranium,
$Y^8$ is molybdenum or tungsten, or is molybdenum and tungsten,
a' is a number in the range from 0.01 to 8,
b' is a number in the range from 0.1 to 30,
c' is a number in the range from 0 to 4,
d' is a number in the range from 0 to 20,
e' is a number greater than 0 in the range from 0 to 20,
f' is a number in the range from 0 to 6,
g' is a number in the range from 0 to 15,
h' is a number in the range from 8 to 16,
x' and y' are numbers which are determined by the valency and frequency of the elements other than oxygen in (II), and
p and q are numbers whose ratio p/q is 0.1 to 10.

In the formula (I), the stoichiometric coefficient b is preferably 2 to 4, the stoichiometric coefficient c is preferably 3 to 10, the stoichiometric coefficient d is preferably 0.02 to 2, the stoichiometric coefficient e is preferably 0 to 5 and the stoichiometric coefficient a is preferably 0.4 to 2. The stoichiometric coefficient f is advantageously 0.5 or 1 to 10.

More preferably, the aforementioned stoichiometric coefficients are all within the preferred ranges mentioned.

In addition, $X^1$ is preferably cobalt, $X^2$ is preferably K, Cs and/or Sr, more preferably K, $X^3$ is preferably tungsten, zinc and/or phosphorus and $X^4$ is preferably Si. More preferably, the variables $X^1$ to $X^4$ all have the aforementioned definitions.

More preferably, all the stoichiometric coefficients a to f and all the variables $X^1$ to $X^4$ have their aforementioned advantageous definitions.

Within the stoichiometries of the formula (I) preference is given to those which correspond to the formula (Ia)

$$Mo_{12}Bi_aFe_bX^1_cX^2_dX^4_fO_n \qquad (Ia)$$

in which
$X^1$ is Co and/or Ni,
$X^2$ is alkali metal,
$X^4$ is Si and/or Al,
a is a number in the range from 0.3 to 1,
b is a number in the range from 0.5 to 10,
c is a number in the range from 2 to 10,
d is a number in the range from 0 to 0.5,
f is a number in the range from 0 to 10, and
n is a number which is determined by the valency and frequency of the elements other than oxygen in (Ia).

Preferably, in the crystalline components of the multimetal oxide of the formula (I), aside from β-$X^1MoO_4$ as the main component, $Fe_2(MoO_4)_3$ is present as a secondary component, and no $MoO_3$ is present.

Among the metal oxides of the formula (Ia), cobalt-containing multimetal oxides have been found to be particularly useful. In a particularly preferred embodiment, the multimetal oxide corresponds to the formula (Ia) in which $X^1$ is Co, $X^2$ is K, $X^4$ is Si, a is a number in the range from 0.5 to 1, b is a number in the range from 1.5 to 3, c is a number in the range from 7 to 8.5, d is a number in the range from 0 to 0.15, f is a number in the range from 0 to 2.5.

Preferably, the composition of the multimetal oxide (Ia) is $Mo_{12}Bi_{0.6}Fe_3Co_7K_{0.08}Si_{1.6}O_n$ and more preferably $Mo_{12}Bi_{0.6}Fe_{2.1}Co_{8.3}K_{0.08}Si_{1.6}O_n$.

Preferably, the multimetal oxide of the formula (Ia) fulfills the following conditions 1, 2 and 3:
  condition 1: 12−c−1.5·13=A where A is a number in the range from 0.5 to 1.5;
  condition 2: the quotient a/A is a number in the range from 0.2 to 1.3;
  condition 3: the quotient c/b is a number in the range from 2.5 to 9.

In multimetal oxides of the formula (II), regions of the chemical composition $[Y^1_a Y^2_b O_{x'}]$ and regions of the chemical composition $[Y^3_c Y^4_d Y^5_e Y^6_f Y^7_g Y^8_h O_{y'}]$ are distributed relative to one another as in a mixture of finely divided $[Y^1_a Y^2_b O_{x'}]$ and finely divided $[Y^3_c Y^4_d Y^5_e Y^6_f Y^7_g Y^8_h O_{y'}]$.

Preference is given to multimetal oxides of the formula (II) comprising three-dimensional regions which differ from their local environment on the basis of their different composition than their local environment and are of the chemical composition $Y^1_a Y^2_b O_{x'}$, and which have a maximum diameter (longest connecting line passing through the center of the region between two points on the surface (interface) of the region) of 1 nm to 100 μm, frequently 10 nm to 500 nm or 1 μm to 50 or 25 μm.

In addition, it is advantageous when at least 25 mol % (preferably at least 50 mol % and more preferably 100 mol %) of the total proportion of $[Y^1_a Y^2_b O_{x'}]_p$ in the multimetal oxides of the stoichiometry (II) is present in the multimetal oxides of the stoichiometry (II) in the form of three-dimensional regions which differ from their local environment on the basis of their different chemical composition than their local environment and are of the chemical composition $Y^1_a Y^2_b O_{x'}$, and which have a maximum diameter in the range from 1 nm to 100 μm.

Advantageous multimetal oxides of the stoichiometry (II) are those in which $Y^1$ is bismuth alone. Among the multimetal oxides of the formula (II), preference is given to those which correspond to the formula (IIa)

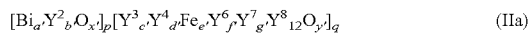

$$[Bi_a Y^2_b O_{x'}]_p [Y^3_c Y^4_d Fe_e Y^6_f Y^7_g Y^8_{12} O_{y'}]_q \quad \text{(IIa)}$$

in which
$Y^2$ is molybdenum or tungsten, or is molybdenum and tungsten,
$Y^3$ is an alkali metal and/or thallium, preferably K, Cs,
$Y^4$ is an alkaline earth metal, nickel, cobalt and/or tin,
$Y^6$ is phosphorus, arsenic, boron, antimony and/or bismuth,
$Y^7$ is titanium, zirconium, aluminum, silicon, copper, silver and/or gold, preferably Si,
$Y^8$ is molybdenum or tungsten, or is molybdenum and tungsten,
a' is a number in the range from 0.1 to 2,
b' is a number in the range from 0.2 to 4,
c' is a number in the range from 0.02 to 2,
d' is a number in the range from 3 to 10,
e' is a number in the range from 0.01 to 5, preferably 0, 1 to 4,
f' is a number in the range from 0 to 5,
g' is a number in the range from 0 to 10, preferably a number greater than 0 in the range from 0 to 10, more preferably a number in the range from 0.2 to 10 and most preferably a number in the range from 0.4 to 3,
x' and y' are numbers which are determined by the valency and frequency of the elements other than oxygen in (IIa), and
p and q are numbers whose ratio p/q is 0.1 to 5, preferably 0.4 to 2.

Among the multimetal oxides of the formula (IIa), preference is given to those in which $Y^2$ is tungsten and $Y^8$ is molybdenum.

Preference is further given to multimetal oxides of the stoichiometry (IIa) comprising three-dimensional regions which differ from their local environment on the basis of their different composition than their local environment and are of the chemical composition $Bi_a Y^2_b O_{x'}$, and which have a maximum diameter (longest connecting line passing through the center of the region between two points on the surface (interface) of the region) of 1 nm to 100 μm, frequently 10 nm to 500 nm or 1 μm to 50 or 25 μm.

Correspondingly, it is advantageous when at least 25 mol % (preferably at least 50 mol % and more preferably at least 100 mol %) of the total proportion of $[Bi_a Y^2_b O_{x'}]_p$ in the multimetal oxides of the stoichiometry (IIa) is present in the multimetal oxides of the stoichiometry (IIa) in the form of three-dimensional regions which differ from their local environment on the basis of their different chemical composition than their local environment and are of the chemical composition $[Bi_a Y^2_b O_{x'}]$, and which have a maximum diameter in the range of 1 nm to 100 μm.

For example, the composition of the multimetal oxide (IIa) is $[Bi_2W_2O_9 \times 2\ WO_3]_{0.50}[Mo_{12}Co_{5.4}Fe_{3.1}Si_{1.5}K_{0.08}O_{y'}]$, $[Bi_1W_2O_{x'}]_{0.5}[K_{0.08}Co_{5.5}Fe_3Si_{1.6}Mo_{12}O_{y'}]$ or $[Bi_1W_2O_{x'}]_{0.4}[K_{0.08}Co_{5.5}Fe_3Si_{1.6}Mo_{12}O_{y'}]$, preferably $[Bi_2W_2O_9 \times 2\ WO_3]_{0.50}[Mo_{12}Co_{5.4}Fe_{3.1}Si_{1.5}K_{0.08}O_{y'}]$.

It is preferably a feature of the multimetal oxide that it has essentially no local centers of element oxides (e.g. iron oxide). Instead, these elements are very substantially part of complex, mixed oxomolybdates. This reduces the unwanted full combustion of organic reaction gas constituents.

The multimetal oxide can be produced by using suitable sources of the elemental constituents thereof (especially other than oxygen) to produce a preferably finely divided intimate dry mixture of a composition corresponding to the particular stoichiometry, and, optionally after compaction (shaping) to give hollow cylindrical shaped bodies, which is optionally effected with use of shaping aids, calcining the latter at temperatures in the range from 350 to 650° C. The calcination can be effected either under inert gas or under an oxidative atmosphere, for example air (or another mixture of inert gas and molecular oxygen), or else under a reducing atmosphere (e.g. a mixture of inert gas, $NH_3$, CO and/or $H_2$) or under reduced pressure. The calcination time may be a few minutes to a few hours and typically decreases with the calcination temperature. Normally, the calcination of the hollow cylindrical shaped catalyst precursor body takes several hours (usually more than 5 h). Frequently, the total calcination time extends to more than 10 h. Preferably, a total calcination time of 45 h or 25 h is not exceeded.

It is preferable to calcine the intimate dry mixture only after completion of compaction. In this case, the hollow cylindrical shaped catalyst body is obtained directly after the calcination. In this respect, the present invention also provides a hollow cylindrical shaped catalyst body obtainable by
(i) producing an intimate dry mixture of sources of the elemental constituents of the multimetal oxide,
(ii) compacting the intimate dry mixture to give a hollow cylindrical shaped precursor body,
(iii) and calcining at temperatures in the range from 350 to 650° C.

Preferably, the intimate dry mixture is compacted by tableting to the hollow cylindrical shaped precursor body.

The term "source" in this document refers to a starting material for preparation of the multimetal oxide.

Useful sources include those compounds which are already oxides of metals present in the metal oxide and/or those compounds convertible to oxides by heating, at least in the presence of oxygen.

As well as the oxides, useful sources are particularly halides, nitrates, formates, oxalates, citrates, acetates, carbonates, amine complexes, ammonium salts and/or hydroxides of metals present in the metal oxide, and hydrates of the aforementioned salts. Compounds such as $NH_4OH$, $(NH_4)CO_3$, $NH_4NO_3$, $NH_4CHO_2$, $CH_3COOH$, $NH_4CH_3CO_2$ and/or ammonium oxalate, which can be broken down and/or decomposed to compounds which escape in gaseous form in the later calcination at the latest, can additionally be incorporated into the intimate dry mixture. Useful substances of this kind, which decompose in the course of calcination, also include organic materials, for example stearic acid, malonic acid, ammonium salts of the aforementioned acids, starches (e.g. potato starch and corn starch), cellulose, ground nutshells and finely ground polymer (e.g. polyethylene, polypropylene etc.).

The intimate mixing of the sources for preparation of the multimetal oxide can be effected in dry form or in wet form. If it is effected in dry form, the sources are appropriately used in the form of fine powders. However, the intimate mixing is preferably effected in wet form.

Advantageously in accordance with the invention, the sources are mixed with one another in the form of solutions and/or suspensions, and the resulting wet mixture is then dried to give an intimate dry mixture. The solvent and/or suspension medium used is preferably water or an aqueous solution.

Particularly intimate dry mixtures are obtained in the above-described mixing process when the starting materials are exclusively sources in dissolved form and/or colloidally dissolved sources of the elemental constituents. Generally, a starting compound may be a source for only one or for more than one of the elemental constituents. Correspondingly, any above-listed source in dissolved form or in colloidal form may have only one or else more than one of the elemental constituents. The drying of the resulting wet mixtures is preferably effected by spray-drying.

The element silicon can be introduced, for example, in the form of a silica sol for production of the wet mixture. Silica sols are colloidal solutions of amorphous silica in water. They have the fluidity of water and do not comprise any sedimentable constituents. The $SiO_2$ content thereof may be up to 50% by weight or more, often over a shelf life of several years (without sedimentation).

A source may also be partly dissolved and partly in colloidal form.

A favorable Mo source is ammonium heptamolybdate tetrahydrate. Further possible Mo sources are ammonium orthomolybdate $((NH_4)_2MoO_4)$, ammonium dimolybdate $((NH_4)_2Mo_2O_7)$, ammonium tetramolybdate dihydrate $((NH_4)_2Mo_4O_{13}\times 5H_2O)$ and ammonium decamolybdate dihydrate $((NH_4)_4Mo_{10}O_{32}\times 2H_2O)$. In principle, however, it is also possible to use molybdenum trioxide, for example.

A preferred K source is KOH (potassium hydroxide). In principle, however, it is also possible to use $KNO_3$ or the hydrate thereof as the K source.

Preferred Bi sources have the Bi in the form of $Bi^{3+}$. Useful Bi sources include, for example, bismuth(III) oxide, bismuth(III)oxide nitrate (bismuth subnitrate), bismuth(III) halide (e.g. fluoride, chloride, bromide, iodide) and especially bismuth(III) nitrate pentahydrate.

The W source used is preferably tungstic acid or the ammonium salts thereof. Tungstic acid, which is essentially insoluble in water, is preferably used here in the form of a finely divided powder. $d_{90}$ of the finely divided powder, appropriately in application terms, is <=5 µm or <=2 µm, preferably 0.1 to 1 µm.

Preferred Fe sources are salts of $Fe^{3+}$, among which particular preference is given to iron(III)nitrate hydrates (cf., for example, DE-A 102007003076). A particularly preferred Fe source is iron(III) nitrate nonahydrate. It is of course also possible to use salts of $Fe^{2+}$ as the Fe source.

To prepare the multimetal oxide, based on the total molar proportion of Fe present therein, at least 50 mol %, better at least 75 mol % and preferably at least 95 mol % is introduced in the form of an Fe source which has the Fe as $Fe^{3+}$. It is also possible to use Fe sources having both $Fe^{2+}$ and $Fe^{3+}$.

Suitable Co sources are the salts thereof having the Co as $Co^{2+}$ and/or $Co^{3+}$. Examples of these include cobalt(II) nitrate hexahydrate, $Co_3O_4$, CoO, cobalt(II) formate and cobalt(III) nitrate. Cobalt(II) nitrate hexahydrate is preferred.

In general, the production of the wet mixture is preferably effected under air (advantageously, the wet mixture is air-saturated). This is especially true when the Co source used and the Fe source used are salts of $Co^{2+}$ and salts of $Fe^{2+}$. This is particularly true when these salts are the nitrates and/or hydrates thereof.

The intimate mixing of the sources for production of the multimetal oxide is preferably effected in wet form, more preferably in aqueous form.

For example, at least one source of the elements Co, Fe and Bi can be used to produce an aqueous solution A. Preferably, the aqueous solution A is an aqueous solution of the nitrates or nitrate hydrates of Co, Bi and Fe. More preferably, the aqueous solution A is an aqueous solution of the nitrates or nitrate hydrates in aqueous nitric acid. Such a solution can also be obtained by dissolving the corresponding metals in aqueous nitric acid.

At least one source of the element Mo and optionally one or more sources of the element K can be used to produce an aqueous solution B.

A preferred Mo source for preparation of an aqueous solution B is ammonium heptamolybdate tetrahydrate $((NH_4)_6Mo_7O_{24}\times 4H_2O)$. If the aqueous solution B comprises K, the source thereof used for preparation of aqueous solution B is advantageously KOH.

The total Co, Fe and Bi content in the aqueous solution A is appropriately, based on the amount of water present in the aqueous solution A, 10 to 25% by weight, advantageously 15 to 20% by weight.

The total Mo content in the aqueous solution B is appropriately, based on the amount of water present in the aqueous solution B, 3 to 25% by weight, advantageously 5 to 15% by weight.

Preferably, the aqueous solution A and the aqueous solution B are mixed with one another. The procedure here is advantageously to stir the aqueous solution A continuously into the aqueous solution B, preferably with vigorous stirring of the initially charged aqueous solution B. The total Mo, Co, Fe and Bi content of the resulting wet mixture of aqueous solution A and aqueous solution B is appropriately, based on the amount of water present in the wet mixture, 5 to 25% by weight, preferably 8 to 20% by weight.

More particularly, for preparation of active compositions of the stoichiometry of the general formula II or IIa, it is advantageous to preform a mixed oxide $Y^1_a Y^2_b O_{x'}$ or $Bi_a Y^2_b O_{x'}$ as a source of the elements $Y^1$, $Y^2$ or Bi, $Y^2$ in the absence of the other constituents of the multimetal oxide.

Preferably, the mixed oxide $Y^1_a Y^2_b O_{x'}$ or $Bi_a Y^2_b O_x$ is preformed by intimately mixing at least one Bi source and at least one W source with one another in an aqueous medium, and drying, for example spray-drying, the aqueous mixture. The dry mass obtained is calcined at temperatures in the range from 400 to 900° C. (preferably 600 to 900° C. and more preferably 700 to 900° C.). Subsequently, the calcined material obtained is divided into a finely divided starting material. This means that the hollow cylindrical shaped catalyst body is obtainable as described above via steps (i), (ii) and (iii), but the formation of the mixed oxide which precedes step (i) can also include a calcination step.

In the preparation of the mixed oxide, the calcination temperature is preferably set such that, on the one hand, a particular phase composition of the calcination product is achieved but, on the other hand, the calcined material has a BET surface area 0.2 m²/g. Desirable phases are $WO_3$ (monoclinic) and $Bi_2W_2O_9$ (orthorhombic); the presence of $\gamma$-$Bi_2WO_6$ (russellite) is undesirable. If, after the calcination, the content of the compound $\gamma$-$Bi_2WO_6$ is more than 5 intensity % (calculated as the ratio of the intensity of the reflection of $\gamma$-$Bi_2WO_6$ in the x-ray powder diffractogram at $2\theta=28.4°$ (CuK$\alpha$ radiation) to the intensity of the reflection of $Bi_2W_2O_9$ at $2\theta=30.0°$, the preparation is preferably repeated and the calcination temperature or the residence time in the case where the calcination temperature remains the same is increased until the limit of 5 intensity % or less is attained.

For preparation of active compositions of the stoichiometry of the general formula II or IIa, it is also advantageous to premix sources of the other constituents of the multimetal oxide in the absence of the elements Bi and W, in order to obtain a premixture of the other constituents. The sources of the other constituents of the multimetal oxide are preferably premixed with one another in the form of solutions and/or suspensions. Solvents and/or suspension media used are preferably water or an aqueous solution.

Preferably, the mixture thus obtained is converted to a dry premixture by drying, preferably spray-drying.

After the preformation, the mixed oxide is combined with the sources of the other constituents of the multimetal oxide, preferably with the premixture of the other constituents, more preferably with the dry premixture of the other constituents, and, optionally after drying, preferably spray-drying, this gives the intimate dry mixture of the sources of the elemental constituents of the multimetal oxide.

If the mixed oxide comes into contact with solvent, especially with water, in the course of production of the intimate dry mixture, it is preferable to ensure that the mixed oxide $Y^1_a Y^2_b O_{x'}$ or $Bi_a Y^2_b O_{x'}$ does not go into solution to a significant extent. A method of production as described above is described in detail in the documents DE-A 4407020, EP-A 835, EP-A 575897 and DE-C 3338380.

If the multimetal oxide comprises the elemental constituents Si, the source used therefor is advantageously aqueous silica sol (cf., for example, DE-A 102006044520), and the latter is advantageously stirred into the wet mixture, it being possible to add water to the wet mixture beforehand. Aqueous silica sol and water are preferably added simultaneously.

In the course of the preparation of the intimate dry mixture, drying steps, preferably spray-drying steps can be effected, as described above, in various processing stages. In the case of spray-drying, the mixture to be dried in the respective processing stage is first divided into fine droplets, and the fine droplets are then dried. Preference is given to spray-drying in a hot air stream. In principle, it is also possible to use other hot gases for spray-drying (e.g. nitrogen or nitrogen-diluted air, or else other inert gases).

This spray-drying can be effected either in a cocurrent or in countercurrent flow of the droplets relative to the hot gas. Typical gas inlet temperatures are in the range from 250 to 450° C., preferably 270 to 370° C. Typical gas outlet temperatures are in the range from 100 to 160° C. The spray-drying is preferably effected in a cocurrent flow of the droplets relative to the hot gas.

Rather than by spray-drying, the mixture to be dried in the respective processing stage can also be dried by conventional evaporative concentration (preferably under reduced pressure; the drying temperature will generally not exceed 150° C.). In principle, the drying can also be effected by freeze-drying.

In principle, the intimate dry mixture can be calcined as such. Frequently, however, the intimate dry mixture is too finely divided for direct calcination.

The intimate dry mixture can be coarsened by subsequent compaction (generally to a particle size of 100 μm to 1 mm). Subsequently, the coarsened powder can be used to shape the hollow cylindrical shaped precursor body, preceded by another addition of finely divided lubricant if required. Such a compaction for the purpose of particle coarsening can be effected, for example, by means of a compactor from Hosokawa Bepex GmbH (D-74211 Leingarten), of the K 200/100 compactor type.

In order to achieve a high mechanical stability of the hollow cylindrical shaped catalyst body, the compaction is controlled such that the coarsened powder particles obtained have a bulk density well below the target density of the shaped, uncalcined hollow cylindrical shaped precursor body. In other words, further compaction of the coarsened powder particles is effected in the course of shaping, for example by tableting.

If the compaction is effected under dry conditions, the compaction may be preceded by mixing, for example, of finely divided graphite and/or other shaping aids mentioned in this document (e.g. lubricants and/or reinforcers) with the intimate dry mixture (for example with a drum-hoop mixer). For example, the compaction can be conducted with a calender having two contra-rotating steel rollers. Subsequently, the compactate can be comminuted, specifically to the particle size appropriate for the envisaged further use, to give a finely divided precursor material. This can be effected, for example, by forcing the compactate through a screen having defined mesh size.

Compaction can in principle also be effected under moist conditions. For example, the intimate dry mixture can be kneaded with addition of water. After the kneading, the kneaded mass, in accordance with the subsequent use, can be comminuted again to the desired level of fineness (cf., for example, DE-A 10049873) and dried to give a finely divided precursor material.

The finely divided precursor materials obtainable as described can then be calcined as such, or first shaped to hollow cylindrical shaped precursor bodies and then calcined.

If the finely divided precursor material is calcined as such, it is then possible to produce a hollow cylindrical shaped catalyst body by compacting it to the hollow cylindrical form (for example by tableting or extruding), with optional addition of auxiliaries, for example graphite or stearic acid as lubricants and/or shaping aids and reinforcers such as microfibers of glass, asbestos, silicon carbide or potassium titanate.

Preferably, the intimate dry mixture is shaped by compaction to hollow cylindrical shaped precursor bodies, and the hollow cylindrical shaped precursor bodies are converted by calcination to the hollow cylindrical shaped catalyst bodies.

This procedure is preferred especially when the intimate mixing of the sources of the elemental constituents of the multimetal oxide to give the finely divided intimate dry mixture is effected in wet form (cf., for example, WO 2008/087116 and DE-A 102008042060).

Shaping aids which may be added include, for example, lubricants, for example graphite, carbon black, polyethylene glycol, polyacrylic acid, stearic acid, starch, mineral oil, vegetable oil, water, glycerol, cellulose ether, boron trifluoride and/or boron nitride. Further useful shaping aids include reinforcers such as microfibers of glass, asbestos, silicon carbide or potassium titanate, which, after the compaction has ended, have a beneficial effect on the integrity of the resulting shaped precursor body. Use of lubricants in the context of a corresponding compaction operation can be found, for example, in documents DE-A 102007004961, WO 2008/087116, WO 2005/030393, US-A 2005/0131253, WO 2007/017431, DE-A 102007005606 and in DE-A 102008040093.

Preferably, exclusively finely divided graphite is used as a lubricant. Useful finely divided graphites for use are especially those recommended in documents WO 2005/030393, US-A 2005/0131253, WO 2008/087116 and DE-A 102007005606. This is especially true of those graphites which are used in the examples and comparative examples in these documents. Very particularly preferred graphites are Asbury 3160 and Asbury 4012 from Asbury Graphite Mills, Inc., New Jersey 08802, USA and Timrex® T44 from Timcal Ltd., 6743 Bodio, Switzerland. Based on the composition to be shaped to give the solid shaped catalyst precursor body, a total of generally ≤15% by weight, usually ≤9% by weight, in many cases ≤5% by weight, often ≤4% by weight, of graphite to be used in accordance with the invention is added.

Based on the weight of the intimate dry mixture, it may comprise, for example, up to 15% by weight of finely divided lubricant (e.g. graphite). Usually, the lubricant content, however, is not more than 9% by weight, in many cases not more than 5% by weight, often not more than 4% by weight, especially when the finely divided lubricant is graphite. In general, the aforementioned added amount is at least 0.5% by weight, usually at least 2.5% by weight.

In general, the compaction to give the hollow cylindrical shaped precursor body is effected by reaction of outside forces (pressure) on the dry mixture. The shaping apparatus to be employed, and the shaping method to be employed, are not subject to any restriction.

For example, the compaction can be effected by extrusion or tableting. This is preferably done using the intimate dry mixture when it is dry to the touch. It may, however, comprise, for example, up to 10% of its total weight of substances which are liquid under standard conditions (25° C., 1 atm (1.01 bar)). The intimate dry mixture may also comprise solid solvates (e.g. hydrates) including such liquid substances in chemically and/or physically bound form. The intimate dry mixture may also be entirely free of such substances.

The preferred shaping process is tableting. The principles of tableting are described, for example, in "Die Tablette", Handbuch der Entwicklung, Herstellung and Qualitätssicherung ["The Tablet", Handbook of Development, Production and Quality Assurance], W. A. Ritschel and A. Bauer-Brandl, 2nd edition, Edition Verlag Aulendorf, 2002, and are applicable to the tableting of the intimate dry mixture.

An example of a useful apparatus for the shaping to give the hollow cylindrical shaped catalyst precursor body is a Kilian RX 73 or S 100 rotary tableting press (from Kilian in D-50735 Cologne). Alternatively, it is possible to use a Korsch PH 800-65 tableting press (D-13509 Berlin).

In the course of tableting, the ambient temperature for the tableting machine is normally 25° C. Appropriately in application terms, the particle diameter of the intimate dry mixture, optionally as a result of a pre-coarsening operation by compaction, is in the range of 100 to 2000 µm, preferably 150 to 1500 µm, more preferably 400 to 1250 µm, or 400 to 1000 µm, or 400 to 800 µm (shaping aid mixed in prior to the compaction is not taken into account here). The shaping pressures are advantageously 50 to 5000 kg/cm$^2$, preferably 200 to 3500 kg/cm$^2$, more preferably 600 to 2500 kg/cm$^2$.

The hollow cylindrical shaped precursor bodies preferably have a minimum residual moisture content.

Preferably, the residual moisture content of the hollow cylindrical shaped precursor bodies is not more than 10% by weight, better not more than 8% by weight, even better not more than 6% by weight, and at best not more than 4% by weight or not more than 2% by weight (the residual moisture content can be determined as described in "Die Bibliothek der Technik" ["Library of Technology"], volume 229, "Thermogravimetrische Materialfeuchtebestimmung", Grundlagen and praktische Anwendungen ["Thermogravimetric Material Moisture Content Determination", Principles and Practical Applications], Horst Nagel, moderne Industrie publishers (for example with the aid of a Computrac MAX 5000 XL from Arizona Instruments)).

Against this background, spray-drying of the wet mixture should be conducted in such a way that the resulting intimate dry mixture has a minimum residual moisture content.

Hollow cylindrical shaped precursor bodies should as far as possible be stored with exclusion of ambient air (having air humidity) (storage until calcination is preferably effected under anhydrous inert gas or under air which has been dried beforehand).

Advantageously, the compaction of the intimate dry mixture is conducted with exclusion of ambient air (having air humidity) (for example under $N_2$ atmosphere).

The calcination of the hollow cylindrical shaped precursor bodies (or generally of uncalcined finely divided precursor material or shaped support bodies coated therewith) is effected normally at temperatures which reach or generally exceed at least 350° C. Normally, in the course of calcination, the temperature of 650° C., however, is not exceeded (the term "calcination temperature" in this document means the temperature present in the calcination material). Preferably, in the course of calcination, the temperature of 600° C., preferably the temperature of 550° C. and frequently the temperature of 500° C. is not exceeded. In addition, in the course of the above calcination, preferably the temperature of 380° C., advantageously the temperature of 400° C., particularly advantageously the temperature of 420° C. and most preferably the temperature of 440° C. is exceeded.

The calcination period can also be divided into several sections. Preferred temperature windows for final calcination temperature are within the temperature range from 400° C. to 600° C., preferably 420 to 550° C., more preferably 440 to 500° C.

The calcination time is generally not more than 10 h. Usually, the duration of 45 h, or 25 h, is not exceeded. The duration is often below 20 h. In principle, a shorter calcination is generally effected at higher calcination temperatures than at lower calcination temperatures.

The calcination time within the temperature range from 430° C. to 500° C. preferably extends to 10 to 20 h.

Preferably, the calcination is preceded by a thermal pretreatment at temperatures in the range from 120° C. to 350° C., preferably 150° C. to 320° C., more preferably 220° C. to 290° C. Such a thermal pretreatment is appropriately conducted until the constituents which break down to gaseous compounds under the conditions of the thermal pretreatment have substantially (preferably completely) been decomposed to gaseous compounds (the time required for this may, for example, be 3 h to 10 h, frequently 4 h to 8 h). The thermal pretreatment is preferably effected under conditions under which the maximum relative decrease in mass of the shaped catalyst precursor body (i.e. the change in mass based on the mass of the shaped catalyst precursor body) does not exceed a value of 1% per minute. Higher maximum relative mass decreases can impair the mechanical stability of the shaped catalyst body, for example through cracking by the breakdown gases which form in the shaped catalyst precursor body. The conditions for the thermal pretreatment include especially the temperature, the rate of temperature increase, the composition of the surrounding gas atmosphere and the convection of the surrounding gas atmosphere.

Both the calcination and the thermal pretreatment which precedes the calcination can be effected either under inert gas or under an oxidative atmosphere, for example air (or a mixture of inert gas and molecular oxygen), or else under reducing atmosphere (e.g. a mixture of inert gas, $NH_3$, CO and/or $H_2$ or under methane, acrolein, methacrolein). The calcination and/or the thermal pretreatment can also be performed under reduced pressure. The atmosphere can also be varied over the course of the calcination and/or the thermal pretreatment.

Preferably, the calcination and optionally also the thermal pretreatment which precedes the calcination are effected in an oxidizing atmosphere. Appropriately, this consists predominantly of stationary or (preferably) moving air (more preferably, an air stream flows through the calcination material). However, the oxidizing atmosphere may likewise consist of a stationary or moving mixture of, for example, 25% by volume of $N_2$ and 75% by volume of air, or 50% by volume of $N_2$ and 50% by volume of air, or 75% by volume of $N_2$ and 25% by volume of air (an atmosphere of 100% by volume of $N_2$ is likewise possible).

In principle, the calcination and optionally also the thermal pretreatment which precedes the calcination can be conducted in a wide variety of oven types, for example heatable air circulation chambers (air circulation ovens, e.g. air circulation shaft ovens), staged ovens, rotary tube ovens, belt calciners or shaft ovens. Preference is given to using a belt calcining apparatus as recommended by DE-A 10046957 and WO 02/24620. Hotspot formation within the calcination material is very substantially avoided by virtue of elevated volume flow rates of calcination atmosphere being conveyed through the calcination material on a gas-permeable conveyor belt which bears the calcination material with the aid of ventilators.

In the course of calcination and optionally also in the course of the thermal pretreatment which precedes the calcination, shaping aids may be conserved or converted to gaseous compounds which escape (e.g. CO, $CO_2$).

The hollow cylindrical shaped catalyst bodies may comprise finely divided inert diluent materials. Suitable finely divided inert diluent materials of this kind include element oxides which have been fired at high temperatures and are comparatively low in pores as a result, such as aluminum oxide, silicon dioxide, thorium dioxide and zirconium dioxide. It is also possible for finely divided silicon carbide or finely divided silicates such as magnesium silicate and aluminum silicate or steatite to be present in the shaped catalyst bodies as inert diluent materials. The calcined multimetal oxide can be ground to a finely divided powder, which can be mixed with finely divided diluent material, and the mixed powder thus obtained can be shaped to a hollow cylindrical shaped body by employing a shaping process presented in this document (preferably by tableting). By subsequently calcining this shaped body once again, the hollow cylindrical shaped catalyst body is then obtained.

The finely divided inert diluent material can alternatively also be incorporated into the wet mixture prior to the drying thereof. In addition, finely divided inert diluent material can be incorporated into a finely divided dry mixture of sources of the elemental constituents of the multimetal oxide. However, such procedures are less preferred.

The specific surface area of the hollow cylindrical shaped catalyst bodies is advantageously 2 to 20 or 15 $m^2/g$, preferably 3 to 10 $m^2/g$ and more preferably 4 to 8 $m^2/g$. The total pore volume is advantageously within the range from 0.1 to 1 $cm^3/g$ or to 0.8 $cm^3/g$, preferably within the range of 0.1 to 0.5 $cm^3/g$ and more preferably within the range of 0.2 to 0.4 $cm^3/g$.

All figures in this document for specific surface areas of solids relate to determinations to DIN 66131 (Determination of specific surface area of solids by gas adsorption using the method of Brunauer, Emmett and Teller (BET)), unless explicitly mentioned otherwise.

Preferably, the contribution of pores having a pore radius of not more than 0.1 μm to the total pore volume is not more than 0.05 $cm^3/g$. If the contribution of such comparatively narrow pores to the total pore volume is more than 0.05 $cm^3/g$, an increase in the calcination time and/or the calcination temperature can bring about an advantageous reduction in this contribution.

Preferably, the contribution of pores having a radius in the range from 0.2 to 0.4 μm to the total pore volume, based on the total pore volume, is at least 70% by volume, advantageously at least 75% by volume, particularly advantageously at least 85% by volume.

All figures in this document relating to total pore volumes and to pore diameter distributions for these total pore volumes are based on determinations by the method of mercury porosimetry using the Auto Pore 9500 instrument from Micromeritics GmbH, D-41238 Moenchengladbach (range 0.003-300 μm).

To determine particle diameter distributions in dry powders and the particle diameters taken therefrom, such as $d_{10}$, $d_{50}$ and $d_{90}$, for example (unless explicitly stated otherwise), the respective fine powder was conducted through a dispersing channel into the Sympatec RODOS dry disperser (Sympatec GmbH, System-Partikel-Technik, Am Pulverhaus 1, D-38678 Clausthal-Zellerfeld), dry dispersed therein with compressed air and blown into the measurement cell in a free jet. Then, according to ISO 13320, the Malvern Mastersizer S laser diffraction spectrometer (Malvern Instruments, Worcestershire WR14 1AT, United Kingdom) was used to determine the volume-based particle diameter distribution therein. The particle diameters $d_x$ reported as the analysis result are defined such that X % of the total particle volume consists of particles having that or a smaller diameter. This means that (100−X) % of the total particle volume consists of particles having a diameter $>d_x$. Unless explicitly stated otherwise in this document, particle diameter determinations and $d_x$ taken therefrom are based on a dispersion pressure of 2 bar absolute employed in the determination (this determining the intensity of the dispersion of the dry powder during the measurement).

The calcined shaped catalyst bodies are preferably stored in 120 l metal drums lined with a flat Lupolen sack having a material thickness of 0.1 mm.

The invention also provides a process for preparing an α,β-unsaturated aldehyde and/or an α,β-unsaturated carboxylic acid by conducting an alkene with molecular oxygen over a fixed catalyst bed comprising a bed of inventive hollow cylindrical shaped catalyst bodies.

The alkene is preferably selected from alkenes having 3 to 6, i.e. 3, 4, 5 or 6, carbon atoms; preferably selected from propene and isobutene. Propene is particularly preferred. Especially useful are polymer-grade propene and chemical-grade propene, as described, for example, by DE-A 102 32 748.

Preferably, the fixed catalyst bed comprises a bed having a plurality of reaction zones. The bed may comprise inert shaped diluent bodies in at least one reaction zone. The proportion of inert shaped diluent bodies in at least two reaction zones may be different. Preferably, the bed in the reaction zone which does not comprise any inert shaped diluent bodies or comprises the lowest proportion of inert shaped diluent bodies comprises inventive hollow cylindrical shaped catalyst bodies. For example, the bed in the reaction zone in which the highest local temperature in the fixed catalyst bed occurs may comprise inventive hollow cylindrical shaped catalyst bodies. In one embodiment of the process, the bed comprises inventive hollow cylindrical shaped catalyst bodies and non-inventive shaped catalyst bodies.

The process is particularly suitable for preparation of α,β-unsaturated aldehydes, especially for preparation of acrolein by gas phase oxidation of propene, and of methacrolein by gas phase oxidation of isobutene. It is preferably a process for preparing acrolein by gas phase oxidation of propene.

The molecular oxygen and the alkene are contacted with the fixed catalyst bed by conducting the molecular oxygen and the alkene over the fixed catalyst bed. Preferably, a reaction gas comprising the molecular oxygen and alkene is conducted over the fixed catalyst bed and thus converted to a product gas.

The molecular oxygen is preferably supplied to the process in the form of air.

The proportion of the alkene present in the reaction gas will generally be 4 to 20% by volume, preferably 5 to 15% by volume, more preferably 5 to 12% by volume, especially preferably 5 to 8% by volume, based in each case on the reaction gas.

Preferably, the reaction gas also comprises at least one inert diluent gas. Inert diluent gases are understood to mean those gases which remain chemically unchanged in the course of the gas phase oxidation to an extent of at least 95 mol %, preferably to an extent of at least 98 mol %. Examples of inert diluent gases are $N_2$, $CO_2$, $H_2O$ and noble gases such as Ar, and mixtures of the aforementioned gases. The inert diluent gas used is preferably molecular nitrogen. The inert diluent gas may comprise, for example, at least 20% by volume, preferably at least 40% by volume, more preferably at least 60% by volume, especially preferably at least 80% by volume and most preferably at least 95% by volume of molecular nitrogen.

Preferably, cycle gas is used as a reaction gas constituent. Cycle gas is understood to mean the residual gas which remains when α,β-unsaturated aldehyde and/or α,β-unsaturated carboxylic acid is removed essentially selectively from the product gas of the gas phase oxidation. In this context, it should be taken into account that the process according to the invention may only be the first stage of a two-stage gas phase oxidation to give the α,β-unsaturated carboxylic acid as the actual target compound, such that the cycle gas is then usually formed only after the second stage. In such a two-stage gas phase oxidation, the product gas of the first stage, optionally after cooling and/or secondary oxygen addition (generally in the form of air), is generally sent to the second gas phase oxidation.

The reaction gas may also comprise at least one further gas constituent. The further gas constituent is preferably selected from CO, methane, ethane, propane, butane, pentane and $H_2$.

The reaction gas preferably comprises alkene:molecular oxygen:inert diluent gas in a volume ratio of 1:(1.0 to 3.0):(5 to 25), preferably 1:(1.5 to 2.3):(10 to 20).

In general, a total pressure of 0.5 to 4 bar, preferably of 1.5 to 3 bar, exists in the reaction gas. All pressure figures in this document relate to absolute pressures.

In general, the load is at least 0.05 l (STP) of alkene/(g of catalyst per h). Preferably, the load is at least 0.08 l (STP) of alkene/(g of catalyst per h), preferably at least 0.08 l (STP) of alkene/(g of catalyst per h) in the case of one temperature zone, preferably at least 0.12 l (STP) of alkene/(g of catalyst per h) in the case of two temperature zones. Preferably, the load is not more than 0.6, more preferably not more than 0.5, further preferably not more than 0.4 and especially preferably not more than 0.35 l (STP) of alkene/(g of catalyst per h). Loads in the range from 0.08 to 0.35 l (STP) of alkene/(g of catalyst per h), preferably 0.14 to 0.35 l (STP) of alkene/(g of catalyst per h) in the case of a plurality of temperature zones, or preferably 0.08 to 0.18 l (STP) of alkene/(g of catalyst per h) in the case of one temperature zone, are particularly appropriate. The load expressed in "l (STP) of alkene/(g of catalyst per h)" corresponds to the alkene volume flow rate (in l (STP) of alkene/h) which is supplied to the reactor, based on the weight of catalyst (in grams) present in the reactor. "l (STP) of alkene" corresponds to the volume of alkene in liters that the alkene supplied would occupy under standard conditions, i.e. at 0° C. and 1 atm (1.01 bar).

In the bed, it is possible for exclusively inventive hollow cylindrical shaped catalyst bodies or else substantially homogeneous mixtures of inventive hollow cylindrical shaped catalyst bodies and shaped diluent bodies to be present. Shaped diluent bodies behave substantially inertly with respect to the heterogeneously catalyzed partial gas phase oxidation. Useful materials for the shaped diluent bodies include, for example, porous or nonporous aluminum oxides, silicon dioxide, zirconium dioxide, silicon carbide, silicates such as magnesium or aluminum silicate, and/or steatite (e.g. of the C220 type from CeramTec, Germany).

The geometry of the shaped diluent bodies may in principle be as desired. In other words, they may, for example, be spheres, polygons, solid cylinders or else hollow cylinders. It is possible to use hollow cylindrical shaped diluent bodies. More particularly, it is possible to use hollow cylindrical shaped diluent bodies whose dimensions essentially correspond to the hollow cylindrical shaped catalyst bodies in the same part of the bed (or reaction zone).

The bed may have one or more reaction zones. A reaction zone is understood to mean a coherent section of the bed which comprises shaped catalyst bodies and in which the composition of the bed is essentially homogeneous. Within a reaction zone too, the bed is only approximately homogeneous, since the hollow cylindrical shaped catalyst bodies and any shaped diluent bodies in the reaction zone are generally aligned randomly and distributed statistically. The individual reaction zones differ from one another in at least one property selected from the content of inert shaped diluent bodies, form of the catalysts, space-filling level of the catalysts, active composition content of the catalysts and chemical composition of the active composition. At least one reaction zone comprises inventive hollow cylindrical shaped catalyst bodies.

Often, the fixed catalyst bed comprises a bed having a plurality of reaction zones, in which case the bed in at least one reaction zone comprises inert shaped diluent bodies, and the proportion of inert shaped diluent bodies in at least two reaction zones is different.

It is favorable to use inventive hollow cylindrical shaped catalyst bodies in at least one reaction zone which does not comprise any inert shaped diluent bodies or comprises the lowest proportion thereof.

In addition, it is favorable to use inventive hollow cylindrical shaped catalyst bodies in the reaction zone having the highest local temperature in the fixed catalyst bed.

Preferably, the fixed catalyst bed comprises two successive reaction zones, and (i) the first reaction zone makes up 25 to 50% of the volume of the fixed catalyst bed. Inventive hollow cylindrical shaped catalyst bodies are used at least in the first reaction zone or in both reaction zones. For example, in the first reaction zone, it is possible to use shaped catalyst bodies having an external diameter of 4 mm, a height of 3 mm and an internal diameter of 2 mm and, in the second reaction zone, to use those having an external diameter of 5 mm, a height of 3 mm and an internal diameter of 2 mm.

Particularly at high loads (>0.12 l (STP) of alkene/(g of catalyst per h)), often also together with the use of a plurality of temperature zones, it is also advantageous to use inventive hollow cylindrical shaped catalyst bodies in the second reaction zone, for example having an external diameter of 4 mm, a height of 3 mm and an internal diameter of 2 mm.

More preferably, the fixed catalyst bed comprises three successive reaction zones, and (i) the first reaction zone makes up 2 to 5% of the volume of the fixed catalyst bed, (ii) the second reaction zone makes up 25 to 45% of the volume of the fixed catalyst bed, and (iii) the third reaction zone makes up 50 to 73% of the volume of the fixed catalyst bed. In the second reaction zone, it is possible with preference to use inventive shaped catalyst bodies, for example having an external diameter of 4 mm, a height of 3 mm and an internal diameter of 2 mm. Particularly in the case of high loads (>0.12 l (STP) of alkene/(g of catalyst per h)), often also together with the use of a plurality of temperature zones, it is also advantageous to use inventive hollow cylindrical shaped catalyst bodies in the third reaction zone, for example having an external diameter of 4 mm, a height of 3 mm and an internal diameter of 2 mm.

The process can be conducted, for example, in a fixed bed reactor having multiple catalyst tubes and one temperature zone, as described, for example, by DE-A 44 31 957, EP-A 700 714 and EP-A 700 893. In such a reactor, a fixed catalyst bed divided between the catalyst tubes is present. Typically, the catalyst tubes in the aforementioned reactors are manufactured from ferritic steel and typically have a wall thickness of 1 to 3 mm. The internal diameter thereof is generally 20 to 30 mm, frequently 21 to 26 mm. A typical catalyst tube length runs, for example, to 3.20 m. Preferably, the number of catalyst tubes accommodated in the shell and tube vessel runs to at least 1000, preferably to at least 5000. Frequently, the number of catalyst tubes accommodated in the reaction vessel is 15 000 to 35 000. Shell and tube reactors having a number of catalyst tubes above 40 000 tend to be uncommon. Within the vessel, the catalyst tubes are normally arranged in homogeneous distribution, in which case the distribution is appropriately selected such that the distance between the central internal axes of mutually adjacent catalyst tubes (called the catalyst tube pitch) is 35 to 45 mm (cf. EP-B 468 290).

The process can also be conducted in a fixed bed reactor having multiple catalyst tubes and several temperature zones, as recommended by DE-A 199 10 506, DE-A 103 13 213, DE-A 103 13 208 and EP-A 1 106 598. A typical catalyst tube length in the case of a fixed bed reactor having multiple catalyst tubes and two temperature zones is 3.50 m. Everything else is essentially as in the fixed bed reactor having multiple catalyst tubes and one temperature zone.

To determine the temperature profile along the fixed catalyst bed in a reaction tube of a shell and tube reactor, it may have a thermowell which runs from the top downward through the center of the reaction tube, in which the temperature can be determined over the entire reaction tube length with the aid of thermocouples run through the thermowell. In principle, any reaction tube present within a shell and tube reactor and charged with the fixed catalyst bed could be modified as described above.

Appropriately in application terms, a shell and tube reactor, however, has only a limited number of thermal reaction tubes of this kind, or else merely "thermal tubes" for short (cf., for example, page 56 of WO 2007/082827, EP-A 873783, EP-A 1270065 and U.S. Pat. No. 7,534,339 B2).

Since thermal tubes, in addition to the fixed catalyst bed, also have to accommodate the thermowells, given otherwise identical tube configuration, they would have an equal heat exchange surface area but a lower free cross section which can be occupied by the fixed catalyst bed than a mere "reaction tube". This is taken into account by configuring them (the thermal tubes) such that the ratio of free cross-sectional area in the tube to the circumference of the tube is the same for thermal tube and reaction tube. Otherwise, reaction tube and thermal tube, given identical tube length, each have the same fixed catalyst bed structure over their tube length. When charging with fixed catalyst bed, it should additionally be ensured that the pressure drop profile established in each case over the tube length in the course of flow of reaction gas mixture through reaction tube or thermal tube is homogeneous in both tube types. Influence can be exerted in a corresponding manner via the rate of filling of the tubes with the shaped bodies and/or through additional use of comminuted (spalled) shaped bodies (cf., for example, EP-A 873783 and U.S. Pat. No. 7,534,339 B2). Overall, it is ensured in this way that a thermal tube and a reaction tube have equal ratios of evolution of heat of reaction in the tube interior and of removal of heat of reaction from the tube interior along the entire tube length. The thermal tube is thus capable of representing the profile of the temperature in the reaction tube for many reaction tubes.

The temperatures measured in the thermal tubes can thus be used to determine the highest local temperature in the fixed catalyst bed and the position thereof in the fixed catalyst bed.

In each temperature zone, a heat exchange medium is conducted around the catalyst tubes between which the fixed catalyst bed has been divided. Preferred heat exchange media are melts of salts such as potassium nitrate, potassium nitrite, sodium nitrite and/or sodium nitrate, or of low-melting metals such as sodium, mercury and alloys of different metals.

The inlet temperature of the heat exchange medium is preferably set to 280° C. to 420° C., preferably to 300° C. to 400° C., more preferably to 320° C. to 380° C.

Viewed over the respective temperature zone, the heat exchange medium can be conducted in cocurrent or in countercurrent relative to the reaction gas mixture. The flow rate of the heat exchange medium within the respective temperature zone is generally selected such that the temperature of the heat exchange medium rises from the entry point into the temperature zone to the exit point from the temperature zone by 0 to 15° C., frequently 1 to 10° C., or 2 to 8° C., or 3 to 6° C. Within the temperature zone, the heat exchange medium is preferably conducted in a meandering manner.

The process can be started up, for example, as described in DE-A 103 37 788 or as described in DE-A 102009047291.

An α,β-unsaturated aldehyde prepared by the process according to the invention can be converted further to the α,β-unsaturated carboxylic acid in a second stage.

By-production of α,β-unsaturated carboxylic acid (acrylic acid, methacrylic acid) accompanying the gas phase oxidation of alkene (propene, isobutene) to give α,β-unsaturated aldehyde (acrolein, methacrolein) is generally undesirable. The products of value (aldehyde and carboxylic acid) can be separated in a later process step.

Examples

Mechanically Stable Hollow Cylindrical Shaped Catalyst Bodies for Gas Phase Oxidation of an Alkene to an Unsaturated Aldehyde and/or an Unsaturated Carboxylic Acid I) Preparation of hollow cylindrical shaped catalyst bodies having the following stoichiometry of the active composition: $[Bi_2W_2O_9 \times 2\ WO_3]_{0.50}[Mo_{12}Co_{5.4}Fe_{3.1}Si_{1.5}K_{0.08}O_x]_1$.

a) Preparation of starting material 1 ($Bi_1W_2O_{7.5}=\frac{1}{2}Bi_2W_2O_9 \times 1\ WO_3$)

In a 1.75 m³ stainless steel jacketed vessel (temperature control water flowed through the interspace) with a crossbeam stirrer, 214.7 kg of tungstic acid at 25° C. (74.1% by weight of W, mean particle size (according to manufacturer determined to ASTM B 330) from 0.4 to 0.8 μm, ignition loss (2 h at 750° C. under air) 6-8% by weight, H. C. Starck, D-38615 Goslar) were stirred (70 rpm) in portions into 780 kg of an aqueous bismuth nitrate solution in nitric acid at 25° C. (11.2% by weight of Bi; free nitric acid: 3 to 5% by weight; prepared with nitric acid from bismuth metal from Sidech S.A., 1495 Tilly, Belgium, purity: >99.997% by weight of Bi, <7 mg/kg of Pb, <5 mg/kg each of Ni, Ag, Fe, <3 mg/kg each of Cu, Sb, and <1 mg/kg each of Cd, Zn) at 25° C. within 20 min. The resulting aqueous mixture was then stirred at 25° C. for another 3 h and then spray-dried. The spray-drying was effected in a Niro FS 15 rotary-disk spray tower in hot air cocurrent at a gas inlet temperature of 300±10° C., a gas outlet temperature of 100±10° C., a disk speed of 18 000 rpm, a throughput of 200 l/h and an air rate of 1800 m³ (STP)/h. The resulting spray powder had an ignition loss of 12.8% by weight (calcine under air at 600° C. for 3 h in a porcelain crucible (which had been calcined to constant weight at 900° C.)) and had (at a dispersion pressure of 1.1 bar absolute) a $d_{50}$ of 28.0 μm ($d_{10}$=9.1 μm, $d_{90}$=55.2 μm).

The resulting spray powder was subsequently converted to a paste with 16.7% by weight (based on the powder) of water at 25° C. in a discharging kneader for 30 min, and kneaded at a speed of 20 rpm and extruded by means of an extruder to extrudates of diameter 6 mm. These were cut into 6 cm sections, dried under air on a 3-zone belt dryer with a residence time of 40 min per zone at temperatures of 90-95° C. (zone 1), 115° C. (zone 2) and 125° C. (zone 3), and then calcined at a temperature in the region of 830° C. (in a rotary tube oven with air flow (reduced pressure 0.3 mbar, 200 m³ (STP)/h of air, 50 kg/h of extrudate, speed: 1 rpm)). The preformed calcined mixed oxide thus obtained was ground with a 500 BQ biplex crossflow classifying mill from Hosokawa Alpine AG, Augsburg, at 2500 rpm, such that the $d_{50}^{41}$ value of the finely divided starting material 1 was 2.8 μm (measured at a dispersion pressure of 2.0 bar absolute), the BET surface area was 0.6 m²/g (measured by nitrogen adsorption after activation under reduced pressure at 200° C. for 4 h) and the γ-$Bi_2WO_6$ content was 2 intensity %, calculated as the ratio of the intensity of the reflection of γ-$Bi_2WO_6$ in the x-ray powder diffractogram at 2θ=28.4° (CuKα radiation) to the intensity of the reflection of $Bi_2W_2O_9$ at 2θ=30.0°. Before the further processing described under c), the finely divided starting material 1 was mixed in portions of 20 kg each in a tilted mixer with mixing and cutting blades (mixing blade speed: 60 rpm, cutting blade speed: 3000 rpm) homogeneously with 0.5% by weight (based on the particular finely divided starting material 1) of Sipernat® D17 finely divided hydrophobized S102 from Degussa (tapped density: 150 g/l; $d_{50}$ of the $SiO_2$ particles (laser diffraction to ISO 13320-1)=10 μm, the specific surface area (nitrogen adsorption to ISO 5794-1, Annex D)=100 m²/g) within 5 min.

b) Preparation of the Starting Material 2 ($Mo_{12}Co_{5.4}Fe_{3.1}Si_{1.5}K_{0.08}O_x$)

A solution A was prepared by metering 1.075 kg of an aqueous potassium hydroxide solution (47.5% by weight KOH) at a temperature of 60° C. and subsequently, via a differential metering balance at a metering rate of 600 kg/h, 237.1 kg of ammonium heptamolybdate tetrahydrate at a temperature of 25° C. (white crystals with a particle size d of <1 mm, 81.5% by weight of $MoO_3$, 7.0-8.5% by weight of $NH_3$, max. 150 mg/kg of alkali metals, H.C. Starck, D-38642 Goslar) into 660 l of water at a temperature of 60° C. in a water-heated 1.75 m³ stainless steel jacketed vessel with a crossbeam stirrer at 60° C. with stirring (70 rpm) within one minute, and the resulting solution was stirred at 60° C. for 60 min (70 rpm).

A solution B was prepared by initially charging a water-heated 1.75 m³ stainless steel jacketed vessel with a crossbeam stirrer at 60° C. with 282.0 kg of an aqueous cobalt(II) nitrate solution at a temperature of 60° C. (12.5% by weight of Co, prepared with nitric acid from cobalt metal from MFT Metals & Ferro-Alloys Trading GmbH, D-41747 Viersen, purity >99.6% by weight, <0.3% by weight of Ni, <100 mg/kg of Fe, <50 mg/kg of Cu), and 142.0 kg of an iron(III) nitrate nonahydrate melt at 60° C. (13.8% by weight of Fe, <0.4% by weight of alkali metals, <0.01% by weight of chloride, <0.02% by weight of sulfate, Dr. Paul Lohmann GmbH, D-81857 Emmerthal) were metered into it with stirring (70 rpm). Subsequently, the mixture was stirred for a further 30 minutes while maintaining the 60° C.

While maintaining the 60° C., solution B was discharged into the initially charged solution A and stirred at 70 rpm at 60° C. for a further 15 minutes. Subsequently, 19.9 kg of a Ludox TM 50 silica sol from Grace at 25° C. (50.1% by weight of SiO$_2$, density: 1.29 g/ml, pH 8.5 to 9.5, alkali metal content max. 0.5% by weight) were added to the resulting aqueous mixture which was then stirred at 70 rpm at 60° C. for a further 15 minutes.

This was followed by spray-drying in a Niro FS-15 rotary disk spray tower in hot air countercurrent at a disk speed of 18 000 rpm (gas inlet temperature: 350±10° C., gas outlet temperature: 140±5° C., throughput: 270 kg/h). The resulting spray powder had an ignition loss of 31% by weight (calcine under air at 600° C. for 3 h in a porcelain crucible (which had been calcined to constant weight at 900° C.)) and had (at a dispersion pressure of 1.1 bar absolute) a d$_{50}$ of 33.0 μm.

c) Production of the Hollow Cylindrical Shaped Catalyst Bodies from the Starting Materials 1 and 2

134 kg of starting material 2 were then initially charged in a tilted mixer (VIL type, fill volume: 200 l, Aachener Misch- and Knetmaschinenfabrik) with mixing and cutting blades (mixing blade speed: 39 rpm, cutting blade speed: 3000 rpm) and premixed for 1 min. Within 10 min, with continued mixing, via a star feeder, starting material 1 was metered thereto in the amount required for a multimetal oxide active material of stoichiometry:

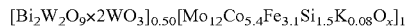

$$[Bi_2W_2O_9 \times 2WO_3]_{0.50}[Mo_{12}Co_{5.4}Fe_{3.1}Si_{1.5}K_{0.08}O_x]_1$$

within 10 min. The mixing operation was then continued for a further 15 min in order to achieve an intensive and complete homogenization (including the breaking apart of any agglomerates present) of the two starting materials. Based on the aforementioned overall composition, 1% by weight of TIMREX T44 graphite from Timcal AG was mixed in within a further 2 min.

The resulting mixture was then compacted in a K200/100 compactor from Hosokawa Bepex GmbH with concave, fluted smooth rollers (gap width: 2.8 mm, roller speed: 9 rpm, target pressing force: approx. 75 kN). Integrated vibrating screens from Allgaier (oversize screen size: 1.5 mm, undersize screen size: 400 μm) with ball-type screening aids (diameter 22 mm) were used to isolate a compactate having a particle size for the most part between 400 μm and 1.5 mm.

For the tableting, a further 2.5% by weight of the TIMREX T44 graphite from Timcal AG were added to the compactate in a turbulent mixer from Drais over the course of 2 min.

Subsequently, the pulverulent aggregate obtained as described was compacted (tableted) under an air atmosphere with the aid of a Korsch PH 865 rotary press (Korsch AG, D-13509 Berlin). Hollow cylindrical shaped bodies having the following dimensions (external diameter×height×internal diameter; in mm) were produced:

4×3×2
4×2×2
5×3×2

The rotation rate of the rotary press was 35 to 45 rpm.

In all cases, the tableting was conducted such that the density of the hollow cylindrical shaped bodies (ratio of tablet mass and tablet volume) was identical and was 2.5 g per milliliter.

For the final thermal treatment, 250 g in each case of each of the hollow cylindrical shaped bodies produced with the different dimensions were installed together on 4 mesh grids arranged alongside one another, each having a square surface area of 150 mm×150 mm (bed height: about 15 mm), in an air circulation shaft furnace (from Nabertherm; furnace model S60/65A) through which air heated to a temperature of 140° C. flowed at 4500 l (STP)/h. Subsequently, the furnace was first heated from room temperature (25° C.) to 130° C. within 72 min. The temperature was measured here by 4 measuring elements, each of which is in the middle of each of the 4 mesh grids, directly within the catalyst bed, and one of these measuring elements provides the actual value for temperature regulation of the furnace. This temperature was maintained for 72 min and then increased to 190° C. within 36 min. The 190° C. was maintained for 72 min, before the temperature was increased further to 220° C. within 36 min. The 220° C. was maintained for 72 min, before the temperature was increased further to 265° C. within 36 min. The 265° C. was maintained for 72 min, before the temperature was increased further to 380° C. within 93 min. The 380° C. was maintained for 187 min, before the temperature was increased further to 430° C. within 93 min. The 430° C. was maintained for 187 min, before the temperature was increased further to the final calcination temperature of 464° C. within 93 min. The final calcination temperature was maintained for 467 min. Thereafter, the furnace was cooled to room temperature within 12 h. For this purpose, the furnace heating and the additional air stream preheating described above were switched off, while maintaining the air flow rate of 4500 l (STP)/h.

II) Gas Phase Oxidation

A reaction tube (V2A steel; external diameter 21 mm, wall thickness 3 mm, internal diameter 15 mm, length 120 cm) was charged from the top downward in flow direction as follows:

Section 1: length about 30 cm
  40 g of steatite spheres with a diameter of 1.5 to 2.0 mm as a preliminary bed.
Section 2: length about 70 cm
  catalyst charge of a homogeneous mixture of 40 g of the hollow cylindrical calcined shaped bodies produced in 1) and 60 g of hollow steatite cylinders (dimensions: 5×3×2; external diameter×height×internal diameter, in mm).

The temperature of the reaction tube was in each case controlled by means of a molecular nitrogen-sparged salt bath having the salt bath temperature T$^{SB}$ of 380° C. (53% by weight of potassium nitrate, 40% by weight of sodium nitrite and 7% by weight of sodium nitrate). The salt bath was within a cylindrical shell. The cylindrical shell had the same length as the reaction tube. The latter was conducted from the top downward within the cylindrical shell such that the two axes of symmetry coincided. The nitrogen stream sparged into the salt bath from the bottom was 40 l (STP)/h. The heat losses of the salt bath to the environment were greater than the heat of reaction produced by the reactor during the partial oxidation. The salt bath was therefore held at its temperature T$^{SB}$ (° C.) by means of electrical heating. In this way, it was ensured that the outer wall of the reaction tube always had the appropriate temperature T$^{SB}$ (° C.).

The reactor was charged continuously with a charge gas mixture (mixture of air, polymer grade propylene and nitrogen) of the composition:
  5% by vol. of propene,
  9.5% by vol. of oxygen and,
  as the remainder to 100% by vol., N$_2$.

The mixed gas flow rate was regulated such that the propene conversion C (based on a single pass of the reaction gas mixture through the reaction tube, in mol %), defined as $$\frac{\text{total number of moles of propene converted}}{\text{total number of moles of propane supplied}} \times 100.$$

was 95.4 mol % at a salt bath temperature of 380° C. The inlet pressure in the reaction tube was 1.2 bar absolute.

Drop Test 50 g of catalyst were allowed to fall through a vertical tube of length 3 m having an internal diameter of 23 mm. The catalyst fell into a porcelain dish directly underneath the tube and was separated from the dust and fractured material which arise on impact. The shaped catalyst bodies separated intact from the dust were weighed. The proportion of intact shaped catalyst bodies was determined by comparison of the mass determined here with the mass of the shaped catalyst bodies used for the drop test (see "Drop test" column in table 1). The proportion of intact shaped catalyst bodies is a measure of mechanical stability of the shaped catalyst bodies. The results are listed in table 1 below.

The load, as a measure of activity, corresponds to the volume flow rate of propene supplied to the reactor (in l (STP)/h) based on the mass of catalyst (in grams) present in the reactor. A higher load corresponds to a higher activity.

The product of value selectivity (mol %) corresponds to the following formula:

$$\frac{\text{number of moles of propene converted to acrolein and acrylic acid}}{\text{number of moles of propene converted}} \times 100.$$

The determination of load and product of value selectivity followed an initial period of more than 7 days, after which activity and product of value selectivity are essentially unchanged over the course of time.

TABLE 1

| Ex. | Shaped catalyst body dimensions (AD[1] × H[2] × ID[3]) [mm] | Load (=activity) [l (STP) of propene/(g of catalyst h)] | Product of value selectivity [mol %] | Drop test [% intact shaped catalyst bodies] |
|---|---|---|---|---|
| 1 | 4 × 3 × 2 | 0.09 | 95.6 | 88 |
| 2 | 4 × 2 × 2 | 0.08 | 95.4 | 91 |
| 3* | 5 × 3 × 2 | 0.06 | 94.9 | 88 |

*)comparative example
[1])external diameter
[2])height
[3])internal diameter

The inventive shaped catalyst bodies are stable (more than 85% intact shaped catalyst bodies in the drop test) and assure a high product of value selectivity of more than 95.3 mol %. In comparative example 3, the product of value selectivity is distinctly inferior to that in inventive examples 1 and 2 (94.9 mol %). The activity of the inventive catalysts is higher (greater than or equal to 0.08 l (STP) of propene/(g of catalyst and hour)) than that of the noninventive catalyst of example 3 (0.06 l (STP) of propene/(g of catalyst and hour)).

The invention claimed is:

1. A hollow cylindrical shaped catalyst body, comprising a compacted multimetal oxide comprising the elements molybdenum, iron and bismuth having an external diameter ED, an internal diameter ID and a height H, wherein
   (i) ED is from 3.5 to 4.5 mm;
   (ii) a ratio q according to the following equation $$q = \frac{ID}{ED}$$

is from 0.45 to 0.55;
   and
   (iii) a ratio p according to the following equation $$p = \frac{H}{ED}$$

is from 0.5 to 0.95
   wherein a ratio of the geometric surface area of the shaped catalyst body to a geometric volume of the shaped catalyst body is from 26 to 30.01 cm$^{-1}$.

2. The catalyst body according to claim 1, wherein ED from 3.7 to 4.3 mm.

3. The catalyst body according to claim 1, wherein p is from 0.65 to 0.9.

4. The catalyst body according to claim 1, wherein a geometric volume of the shaped catalyst body is from 22 to 34 mm$^3$.

5. The catalyst body according to claim 1, wherein a density of the shaped catalyst body is from 1.2 to 2.0 g/cm$^3$.

6. The catalyst body according to claim 1, wherein a value WT according to the following equation $$WT = \frac{ED - ID}{2}$$

is from 0.8 to 1.2 mm.

7. The catalyst body according to claim 1, wherein ED is from 3.7 to 4.3 mm, H is from 2.8 to 3.2 mm and ID is from 1.8 to 2.2 mm.

8. The catalyst body according to claim 1, obtained by a process comprising:
   (i) producing an intimate dry mixture of sources of the elemental constituents of the multimetal oxide,
   (ii) compacting the intimate dry mixture to obtain a hollow cylindrical shaped precursor body,
   (iii) and calcining at a temperature of from 350 to 650° C.

9. The catalyst body according to claim 8, wherein the intimate dry mixture is compacted to the hollow cylindrical shaped precursor body by tableting.

10. The catalyst body according to claim 8, obtained by thermally pretreating the hollow cylindrical shaped precursor body prior to the calcination under conditions under which a maximum relative decrease in mass of the shaped catalyst precursor body does not exceed a value of 1% per minute.

11. A process for preparing an α,β-unsaturated aldehyde an α,β-unsaturated carboxylic acid, or both, comprising contacting an alkene with molecular oxygen over a fixed catalyst bed comprising a bed of hollow cylindrical shaped catalyst bodies according to claim 1.

12. The process according to claim 11, wherein the process obtains acrolein by gas phase oxidation of propene.

13. The process according to claim 11, wherein
the fixed catalyst bed comprises a bed having a plurality of reaction zones,
the bed comprises inert shaped diluent bodies in a reaction zone, and
a proportion of inert shaped diluent bodies in at least two reaction zones is different.

14. The process according to claim 13, wherein a bed in the reaction zone which comprises the lowest proportion of inert shaped diluent bodies, if any inert shaped diluent bodies, comprises the hollow cylindrical shaped catalyst bodies.

15. The process according to claim 13, wherein a bed in the reaction zone in which the highest local temperature in the fixed catalyst bed occurs, comprises the hollow cylindrical shaped catalyst bodies.

16. The process according to claim 11, wherein the bed further comprises other shaped catalyst bodies which are not in accordance with the hollow cylindrical shaped catalyst bodies.

* * * * *